United States Patent [19]

Keydar

[11] Patent Number: 4,707,438
[45] Date of Patent: Nov. 17, 1987

[54] IMMUNOASSAY FOR BREAST CANCER EMPLOYING MONOCLONAL ANTIBODIES

[75] Inventor: Iafa Keydar, Tel Aviv, Israel

[73] Assignees: Tel Aviv University; Teva Pharmaceutical Industries, Limited, both of Tel Aviv, Israel

[21] Appl. No.: 702,055

[22] Filed: Feb. 15, 1985

Related U.S. Application Data

[63] Continuation of Ser. No. 643,279, Aug. 22, 1984, abandoned.

[51] Int. Cl.$^4$ ............... G01N 33/53; G01N 33/574; G01N 33/577
[52] U.S. Cl. .......................................... 435/5; 435/7; 435/21; 435/28; 435/172.2; 435/240.27; 435/948; 436/531; 436/548; 436/804; 436/813; 530/387; 530/808; 935/89; 935/103; 935/110
[58] Field of Search ............... 436/548, 513, 804, 546, 436/540, 529, 503, 813; 435/68, 172.2, 240, 241, 948, 43, 7, 5, 21, 28; 424/85, 86, 87; 260/112 R; 935/89, 103, 106, 108, 110; 530/387, 808

[56] References Cited

U.S. PATENT DOCUMENTS 4,376,110 3/1983 David et al. .................. 436/513
4,522,918 6/1985 Schlom et al. ................. 435/68

OTHER PUBLICATIONS

Taylor-Papadimitriou et al, Int. J. Cancer: 28, 17–21 (1981).
Keydar et al, Europ. J. Cancer: 15, 659–670 (1979).
Keydar et al, Cancer Letters, 17, 37–44 (1982).
Keydar et al, PNAS, 81, 4188–4192 (1984).
Ohno et al, Breast Cancer Research Conference, Mar. 1983, Abstract No. 96, p. 50.
Mesa-Tejada et al, Breast Research Conference, Mar. 1983, Abstract No. 97, p. 5.
Menard et al, Cancer Research, vol. 43, 1295–1300, 1983.
Colcher et al, Proc. Natl. Acad. Sci., vol. 78, No. 5, 3199–3205, 1981.
Spiegelman et al, Cancer, vol. 46, 879–892, 1980.

*Primary Examiner*—Sidney Marantz
*Attorney, Agent, or Firm*—John P. White

[57] ABSTRACT

An immunoassay for diagnosing and monitoring human breast cancer. The assay employs a monoclonal antibody which recognizes a human mammary tumor virus derived from the T47D clone-10 breast cancer cell line (HMTV). The monoclonal antibody is produced by the hybridoma cell line deposited with the American Type Culture Collection under ATCC Accession No. HB 8630.

When the immunoassay is performed on a tissue sample from a subject, the sample is contacted with monoclonal antibody ATCC Accession No. HB 8630 so as to form an antibody-antigen complex between the monoclonal antibody and any HMTV antigens which may be present in the sample. This antibody-antigen complex is then detected employing a second detectable antibody specific to the first monoclonal antibody. The presence or absence of the complex indicates the presence or absence of breast cancer in the subject.

When the immunoassay is performed on a body fluid sample from a subject, the sample is first contacted with a detectable soluble antibody so as to form an antibody-antigen complex between the antibody and any HMTV antigens which may be present in the sample. The fluid sample is then contacted by a second antibody which is attached to a solid support. Either the first or second antibody is the monoclonal antibody produced by hybridoma cell line ATCC Accession No. HB 8630. The presence or absence of the complex indicates the presence or absence of human breast cancer in the subject.

22 Claims, No Drawings ic IMMUNOASSAY FOR BREAST CANCER
EMPLOYING MONOCLONAL ANTIBODIES

This is a continuation of application Ser. No. 643,279, filed Aug. 22, 1984, now abandoned.

BACKGROUND OF THE INVENTION

Throughout this application, various publications are referenced to provide background information concerning the state of the art as known to those of ordinary skill therein as of the date of the invention disclosed and claimed herein. In the text of this application, these publications will be referred to by full citations. The disclosures of these references in their entireties are hereby incorporated by reference into the present application.

Since the discovery of an oncorna virus—the mouse mammary tumor virus (MMTV)—capable of initiating mammary tumors in mice, efforts were made to find a similar agent in the human disease. A great body of evidence was accumulated in the last decade suggesting that human breast tumors are similar to the mouse mammary tumors. The similarities mentioned in the literature refer to particles isolated from human tumors with biochemical and biophysical properties of oncorna viruses. Furthermore, it was demonstrated that human breast tumors contain RNA molecules with detectable amounts of sequence homology to the MMTV.

More direct immunological cross-reactivity between the human tumors and the MMTV was demonstrated by Mesa-Tejada et al. 1978, J. of Histochem. and Cytochem. 26: 532–541. Using the immunoperoxidase technique, they showed that some human breast tumors (212 out of 447 patients) contain an antigen that cross-reacts with the envelope glycoprotein of mouse mammary tumor virus (glycoprotein 52000 dalton MW—gp52). Furthermore, that group was able to demonstrate that the immunological cross-reactivity is due to the protein moiety of this molecule and not to the carbohydrate fraction. These findings were very encouraging in view of the findings obtained in the mouse disease. Spiegelman's group, Ritzi et al., 1976, Virology 75: 188 and Ritzi et al., 1977, J. Exp. Med. 145: 988–1013, have demonstrated that the gp52 viral glycoprotein is an excellent indicator for the mouse disease status. Plasma levels of gp52 measured by radioimmune assay could be correlated with the existence, size and recurrence of the mouse mammary tumor after surgical excision, often without physical sign of the disease.

More recently, Dion et al., 1974, J. Virology 14: 40–46, isolated a human milk protein that is structurally and antigenically related to MMTV gp52. Immunoprecipitation analyses indicated the presence of an antigenically cross-reacting glycoprotein having a MW of about 58,000 daltons. The two glycoproteins shared common sequences when tryptic peptide maps were prepared, but they also differed significantly so that it was clear that the two glycoproteins were not identical.

Further support linking breast cancer and MMTV antigens comes from the finding that the presence of antibodies to murine mammory tumor viral antigen have been reported in the serum of a number of breast cancer patients by Witkin et al., 1980, Int. J. Cancer 25, 721–725.

While this research has important implications for the understanding of the etiology of breast cancer, it has also been of interest because of its potential for diagnosing and monitoring the cause of malignant breast disease.

Spiegelman (U.S. Pat. No. 4,379,839) discloses an immunologic method for assaying the presence of viral related proteins in plasma samples as a way of diagnosing and following breast cancer in humans. Spiegelman's assay utilizes the cross-reactivity of the viral related protein with antibodies directed to Mason-Pfizer Monkey Virus or murine mammary tumor virus. However Spiegelman's test, which does not employ monoclonal antibodies, does not give a very high percentage of clear positive reactions with all breast adenocarcinoma samples.

More recently, Mesa-Tejada et al., Breast Cancer Research Conference, Denver, Colo. Mar. 20–24, 1983 Immunology Poster Abstracts 96–97, reported studies of monoclonal antibodies to RNA virus-like from the T47D breast carcinoma cell line. They reported on ascites form of two monoclonal antibodies ($ASC_2 18$, $ASC_2 26$), to virus-like particles isolated from the T47D clone 11 cells, the first giving 91% positive staining, the latter giving 58% positive staining. However, $ASC_2 18$ gave 63% positive staining in the samples of benign breast tissue tested while $ASC_2 46$ gave 26% positive staining in the samples of benign breast tissue tested. However, such a high rate of false positives, in immunohistochemical assay, is unsatisfactory for diagnosis of breast carcinomas.

Two other research groups have tried to produce McAbs reacting specifically with human mammary tumor-Ag. Papadimitriou et al., 1981, Int. J. Cancer 28: 17–21, isolated three hybridomas producing McAbs against components of the human mammary fat globules. All three Abs showed negative reactions with fibroblasts, lymphoblastoid cells, and a large number of epithelial cell lines of non-breast origin. Eight breast cancer lines were tested and the results obtained were that the two of the Abs reacted with seven breast cell lines, and the third Ab reacted with only two out of the eight breast cell lines. All three McAbs isolated by Papadimitriou bound positively to a pharingeal carcinoma line and a colon carcinoma line; supernatants from two of the three McAbs showed binding to derivatives of HeLa cells (Papadimitriou et al., 1981, Int. J. Cancer 28: 17–21).

Schlom et al., 77: 6841–6845 (1980, Proc. Nat'l, Acad. Sci. (USA) 78: 3199–3203, fused lymphocytes from lymph nodes obtained at mastectomy from breast cancer patients with myeloma cells NS-1 (Balb/c non Ig-secreting myeloma cell line), and obtained hybridoma cultures that synthesized human monoclonal Ab. The immunological reactivities of the human Igs were assayed on tissue sections by using the immunoperoxidase technique. The human Ig M McAb.MBE6, was chosen for extensive anslysis because of its reactivity against human breast carcinomas, and the results obtained were variable: (1) Eighty-one percent of primary malignant mammary tumors and 100% of metastatic breast lesions reacted positively with moderate or strong intensity; (2) fourteen percent of benign breast lesions showed staining; (3) moreover, normal mammary epithelial cells in areas adjacent to primary tumor cells showed staining with the MBE6; (4) preliminary studies also indicated a cross-reactivity between the MBE6 and cells of selected non-breast adenocarcinomas, such as bronchio-alveolar carcinoma of the lung and a medullary carcinoma of the thyroid. As mentioned by Schlom et al., this McAb is not entirely specific to mammary breast tumors since it reacts with a small population of normal breast tissue and other malignant tissues.

Although improvements in immunoassays for human breast cancer have provided increased sensitivity or specificity, or both, it has not been possible until the present invention to obtain a high positive staining rate without having an associated high rate of false positives.

SUMMARY OF THE INVENTION

This invention concerns an immunoassay for use in detecting human breast cancer in a sample of tissues or body fluids. The assay is based on a monoclonal antibody directed to human mammary tumor virus derived from the T47D clone 10 breast cancer cell line. The assay utilizes the monoclonal antibody produced by hybridoma cell line 23 (ATCC No. HB 8630).

According to one aspect of the present invention, the assay involves contacting a sample with first and second antibodies to form an antibody-antigen complex with human mammary tumor virus antigens which may be contained in a sample. One of the two antibodies used in the assay should be detectable, and one of the antibodies should be the monoclonal antibody of the present invention. The presence or absence of detectable antigen in the antibody-antigen complex may be detected or measured using a radioactively labeled antibody, or an enzyme linked antibody. The enzyme allows detection by catalyzing a detectable reaction.

According to one preferred embodiment, the sample may be a tissue sample. The immunoassay is performed by contacting the tissue sample with the monoclonal antibody of the present invention, to allow formation of an antibody-antigen complex with human mammary tumor virus contained in the sample. The sample is also contacted with a detectable antibody, which may be an antibody directed to the monoclonal antibody. The detectable antibody may include a radioisotope label or it may be linked to an enzyme which catalyzes a detectable reaction.

In another preferred embodiment, the immunoassay may be used to help diagnose human breast cancer in a fluid sample, such as blood serum. This embodiment involves contacting a fluid sample with a first soluble antibody, which is labeled and a second antibody attached to a solid matrix. Either the first or second antibodies Should preferably be the monoclonal antibody of the present invention.

DETAILED DESCRIPTION OF THE INVENTION

List of Abbreviations

The following abbreviations will be used herein:
Ab(s)—antibody(ies)
Ag(s)—antigen(s)
AP-GARIG—alkaline phosphatase goat anti-rabbit IgG
cpm—counts per minute
DDW—double distilled water
d-FCS—dialyzed fetal calf serum
ELISA—enzyme-linked immunosorbent assay
FCS—fetal calf serum
HAT—Hypoxanthine, aminopterin, thymidine
HMTV(47D)-clone 10—human mammary tumor virus of the T47D cell line subline 10
HS—horse serum
Ig(s)—Immunoglobulin(s)
McAb(s)—monoclonal antibody or antibodies
MMTV—murine mammary tumor virus
NHP—normal human plasma
NMS—normal mouse serum
NRS—normal rabbit serum
OD—optical density
Po-R MIgG—peroxidase-linked rabbit anti-mouse IgG
PBS—phosphate buffered saline
PEG—polyethylene glycol
rpm—revolutions per minute
RSV—Rous sarcoma virus
SSV—Simian sarcoma virus
MPMV—Mason Pfiser Monkey virus
MULV—Murine leukemia virus
CEA—Carcinoembryonic antigen
hCG—human choriogonadotropin Recent improvements in immunoassay technology, particularly the development of monoclonal antibodies, have permitted improvements in the sensitivity of assays for human breast cancer. However, until the present invention, assays have not been available which possess essentially absolute specificity for human breast cancer, having no cross-reaction with malignancies of non-breast origin or other undesirable false positives.

Specifically, this invention provides an immunoassay for detecting human breast cancer in a sample of tissue or body fluids. The immunoassay includes a monoclonal antibody directed to the human mammary tumor virus derived from the T47D clone 10 breast cancer cell line. This is a human breast cancer cell line which has been established from the pleural effusion of a patient with intraductal and invasive carcinoma of the breast (Keydar et al., 1979, Europ. J. Cancer 15: 659–670). The monoclonal antibody is derived from hybridoma 23. The monoclonal antibody produced from this hybridoma are in the $\gamma_1$ subclass, and "recognize" the human mammary tumor virus from T47D-clone 10, but lack reactivity with other retroviruses such as MMTV, SSV, MPMV, RSV, and MULV, and with other human proteins tested. This hybridoma cell line has been deposited with the American Type Culture Collection in Rockville, Md. 20852 U.S.A. under ATCC No. HB 8630. This deposit was made pursuant to the provisions of the Budapest Treaty on the International Recognition of the Deposit of Microorganisms.

The invention concerns an immunoassay useful in the diagnosis of human breast cancer. The immunoassay involves contacting a sample, such as a tissue or body fluid sample believed to contain human mammary virus antigens, with first and second antibodies to form an antibody-antigen complex with human mammary tumor virus antigens. One of the first or second antibodies should be the monoclonal antibody of the present invention. The other antibody varies depending on the particular assay being done. It may be an antibody directed to the monoclonal antibody of the present invention, in the assay involving a tissue sample, or it may be another antibody directed to the human mammary tumor virus. It may also be a monoclonal antibody from the same or a different hybridoma strain.

The presence or absence of labeled or detectable antibody included in the complex may be detected or measured by various techniques, depending on the particular immunoassay and label used. For example, radioactive labels may be detected by scintillation counting, radiography, or other methods which can detect radioactive decay after separating the unreacted detectable antibody. If an enzyme linked immunoassay is used, the presence of enzyme labeled antibody in the antibody-antigen complex can be detected after removing unreacted enzyme labeled antibody. A substrate is added which produces a colored precipitate on contact with the enzyme. The presence of color can be detected or measured spectrophotometrically, for example, to determine the presence or amount of antigen.

In one preferred embodiment, the assay is performed on a tissue sample. This tissue sample may be taken from breast tissue or it may come from tissue such as a metastatic lesion, elsewhere in the body. By assaying non-breast tissues with the monoclonal antibodies of the present invention, it may be determined whether a lesion in non-breast tissue is a breast tumor metastasis, thereby enabling the clinician to monitor the progress of the disease, and the effectiveness of any treatment protocol, a significant advantage of the present invention. The assay for breast cancer in a tissue sample involves contacting a tissue sample with the monoclonal antibody of the present invention. Thereafter, the tissue sample is contacted with a second detectable antibody which is directed to the monoclonal antibody. The detectable antibody may be radioactively labeled or may be linked to an enzyme which catalyzes a detectable reaction. Preferably, before determining the presence or absence of detectable antibody attached to the tissue sample, the tissue sample should be separated from unreacted detectable antibody.

When the assay is carried out in a tissue sample, the detectable antibody should preferably be a conjugate between horseradish peroxidase or other suitable enzymes and rabbit anti-mouse immunoglobin. The antibody may also be radioactively labeled, preferably with $^{125}I$. Other detection methods known in the art may also be used including fluorimetry involving fluorogenic labels.

In another preferred embodiment, the immunoassay of the present invention provides a method for the detection of human breast cancer by assaying a fluid sample for human mammary tumor viral related protein. The fluid sample is preferably blood serum, but it may also be pleural fluid, or ascitic fluid.

This immunoassay involves contacting a fluid sample with a first antibody which is preferably soluble and detectable to form an antibody-antigen complex with the antigenic substance contained in the sample. The complex is contacted with a second antibody to the same antigenic substance. One of the two antibodies should be the monoclonal antibody of the present invention, while the other antibody can be the same type or another monoclonal antibody or affinity purified rabbit antibody directed to the same antigenic substance.

This invention also contemplates using the improved monoclonal antibody of the present invention in immunoassays known in the art. For example, the monoclonal antibody can be used in sandwich assays, as disclosed by David et al., U.S. Pat. No. 4,376,110, which is an example of a heterogeneous immunoassay, or in homogeneous immunoassays such as those disclosed in an article by Bogulaski and Li, "Homogeneous Immunoassays," in Applied Biochemistry and Biotechnology, Vol. 7, pp. 401–414 (1982). Homogeneous assays, unlike their heterogeneous counterparts, do not require separation of bound antibody from free analyte because the activity of the label is modulated by antibody binding.

The following section "EXPERIMENTAL DETAILS" is set forth to aid in understanding of the present invention but is not intended, and should not be construed, to limit the invention as defined by the claims which follow thereafter.

EXPERIMENTAL DETAILS

Example 1

The Antigen: Viral Particles from T47D (HMTV)

The cell line T47D was derived from epithelial pleural effusion cells of a breast cancer patient as described by Keydar et al., 1979, Europ, J. Cancer 15: 659–670.

The human mammary tumor virus-like particles (HMTV) were obtained by induction with steriod hormones as described by Keydar et al., 1982, Cancer Letters 17: 37–44, and Keydar et al., 1983, Proc. Nat'l Acad. Sci. (USA). in press.

This HMTV contain antigens which cross-react immunologically with the glycoprotein of MMTV (gP 52) (Mesa-Tejada et al., 1978, J. of Histochem. and Cytochem. 26: 532–541).

In order to obtain a cell population of the highest homogeneity as well as the best viral production, the T47D cells were cloned by the classical soft agar technique.

Isolation of Single Cell Clones

Several different cloned sublines were isolated from the T47D cell line by this technique. The sublines were designated as clones 5, 8, 10, 11 and 19. The highest production of viral particles was obtained with clone 10. Therefore, this clone serves as a source for virus production in vitro.

Identification of the T47D Retroviral Particles

The release of viral particles was monitored by the extent of incorporation of 3H-uridine in the viral RNA, as described by Keydar et al., 1983, Proc. Nat'l. Acad. Sci (USA). in press.

Purification of the T47D Particles from Culture Medium

Approximately 5 liters of cell free culture supernatant stored at −70° C. was thawed and concentrated down to 100 ml with the Pellicon cassette system of Millipore and centrifuged at 100,000×g for 90 min. at 4° C. in a Spinco SW 27 rotor. The resulting pellets were resuspended in approximately 5 ml of TNE (0.01M Tris-HCl, 0.15M NaCl, 3 mM EDTA) pH 7.6 and layered over linear 20–50% sucrose in TNE gradients. The samples were centrifuged as above for 16 hrs. and 25 fractions of equal volume were collected from below and the density of each fraction was determined with a Zeiss refractometer. The fractions of the density region between 1.16 and 1.20 ug/ml (in which RNA tumor viruses localized) were pooled, diluted, and centrifuged as above for 90 min. The resulting pellets were resuspended in 0.6 ml of Pi/NaCl.

Production of Antibodies Against HMTV Particles, Released by Clone-10 (T47D) Cells Rabbit antisera against HMTV were prepared by immunizing New Zealand white rabbits with the purified disrupted viral particles. The purified immunogloulin preparation was preabsorbed on normal human plasma to eliminate traces of antibody activity with normal human components.

These antibodies were used as serological probes in detection of breast cancer (Keydar, Israel patent app. 60987) but were of only limited value. Greater reactivity and specificity could be achieved through the use of monoclonal antibodies that react with single antigenic determinant.

Monoclonal Antibodies

The monoclonal antibody against the HMTV (T47D)-clone 10 has proven extremely useful in the immunohistochemical identification of breast carcinoma tissue in 91% (out of 366 biopsy-proven breast carcinomas) with no positive staining in either benign breast tissue or in non-breast carcinomas including kidney, colon, lung, ovary, prostate, liver, skin and thyroid. The same monoclonal antibodies were used in a sensitive ELISA method for assaying the level of the corresponding antigen in body fluid.

Preparation of Monoclonal Antibodies Against Viral Proteins of T47D-Clone-10

Balb/c mice were used for immunization with the RMTV (T47D) Ag since all the murine myelomas adequate for fusion were derived from this mouse strain. The mice were two months old. The immunization regimen used was: HMTV (T47D) clone-10 particles were dissociated in opening buffer (2 parts of virus in 1 part opening buffer) for 30 min. at 37° C., and then diluted tenfold with PBS. Opening Buffer: 540 mg urea, 15 mg Deoxychlorate, 300 µl 10% Triton×100, 700 µl DDW.

Adjuvant: Complete Feund's Adjuvant-(CFA) (DIFCO); Incomplete Freund's adjuvant-(IFA).

Preparation of Emulsion: The Ag solution was thoroughly mixed with 1.5 volumes of CFA.

Immunization Protocol:

| time of immunization (weeks) | 0 | 3 | 7 | after one day |
|---|---|---|---|---|
| Antigen | 100 µg | 100 µg | 20-50 µg | 20-50 µg |
| Adjuvant | CFA | IFA | IFA | — |
| Route of injection | ID | ID | IP | IV |

ID - intra dermal; IP - intra peritoneal; IV - intra venous

Ten to fourteen days after the second injection, the mice were bled and the titer of the relevant Ab was detetermined by ELISA. Only those who showed the highest Ab titer were selected. Three days after the IV boost (usually given in the tail), the spleen was removed and the cells used for fusion.

Growth of Myeloma Cell Lines: The myeloma cell line employed was NS-1, which is a non-producing immunoglobulin myeloma, and has a very high cloning efficiency. This myeloma cell line has genetic deficiencies which do not allow cells to grow under certain conditions. Thus, they lack the enzyme hypoxanthine guanine ribosyl transferase and/or thymidine kinase. The mutants are usually selected among those able to grow in the presence of 8-AG. Such mutants are resistant to those DNA analogues, because they lack the enzymes of the salvage pathway. For the same reason they are unable to incorporate externally supplied hypoxanthine and/or thymidine. When endogeneous synthesis of DNA precursors is blocked with aminopterin, the cells die, even when hyproxanthine and thymidine are also included (HAT media). Hybrids between myeloma cells and spleen cells (which contain the wild type salvage pathway enzymes) can then be selected from the parental components as the only cells that actively multiply in HAT medium. The cells were grown in DMEM supplemented with 15% HS, and were maintained in a 7-10% $CO_2$+air at 37° C. humid incubator in stationary suspension culture. To avoid revertants, we occasionally grew the cells in the presence of 8-AG (20 µg/ml) and checked whether all die in HAT medium.

Fusion of Mouse Cells with PEG

Parental Cells

Myeloma Cells:
NS-1 cells were grown in the presence of 8-AG in a few weeks before fusion. A week prior to fusion the 8-AG is removed.

Immune Spleen Cells:
Balb/c mice which were immunized according to the protocol, were bled to death just before fusion and the serum kept at −20° C.

Preparation of Cells

Spleen Cells:
(a) The spleen was removed from the mouse in a sterile hood into DMEM serum-free medium in a Petri dish, and was rinsed twice.

(b) Spleen were teased apart with sterile forceps, resuspended and transferred to 10 ml capped conical tubes which were left in a vertical position for 10 min. on ice to let large pieces of tissue settle down.

(c) Suspensions were transferred to new 10 ml conical tubes, the cells spun down at 200×g at room temperature (RT) for 10 min. and the pellet resuspended in DMEM serum free. An aliquot was removed for total cell counting (Diluted 1:10 in 0.1% trypan blue), and the cells were spun and resuspended in the same volume of serum free DMEM.

Myeloma cells:
(a) NS-1 cells were removed from the flasks into 50 ml conical tubes, an aliquot was removed for counting (diluted 1:2 with 0.1% trypan blue).

(b) The cells were spun at 200×g for 10 min. at RT, and resuspended in DMEM to $2\times10^7$ NS-1 cells/ml.

Procedure for Cell Fusion (a) Spleen cells and myeloma cells at a ratio of 5:1 were mixed and DMEM was added to a final 40 ml volume. After centrifugation, the supernatants were removed by careful aspiration and the tubes gently flicked in order to loosen the cell pellet.

(b) One ml of prewarmed (37° C.) 50% PEG was added dropwise with a wide opening pipette, and the cell pellet was gently resuspended for one minute, and incubated for another minute at 37° C.

(c) Prewarmed DMEM was added dropwise to dilute the PEG; the addition was done very slowly with gentle mixing of cells as follows: 5 ml medium the first 5 min., then 10 ml the next 5 min., and additional 20 ml of DMEM the last 5 min.

(d) The mixture was centrifuged at 200×g and the supernatant removed. Five ml of HAT medium was added very cautiously in order to resuspend the cells. An aliquot was taken to count the number of viable NS-1 cells, which appear larger than most of the spleen cells (if the viability is less than 20%, another fusion should be done).

(e) The fused cells were resuspended to a concentration of $2-5\times10^5$ viable NS-1 cells/ml, in HAT medium, and distributed as 100 µl aliquots in the wells of a 96 well microculture plate (Falcon).

(f) After 4-5 days of incubation, 100 μl of prewarmed HAT medium was added to each well. Eight to ten days following the fusion, the cultures were fed by aspirating half of the culture fluid and replacing it with fresh prewarmed HAT medium.

(g) The cultures were inspected for hybrid cell growth. When vigorous growth and change of medium color to yellow was observed, supernatants were removed and screened for Ig secretion.

(h) Positive cultures were transferred each into one well of 24-well plates, and then to small (25 cm$^3$) culture flasks (Sterilin).

(i) The hybrid cells secreting the specific Ab (as checked by ELISA) were frozen with 10% glycerol in the culture medium at $-70°$ C., or in liquid nitrogen, as early as possible. In parallel, cloning of the cells was performed to ensure monoclonality.

Cloning of Cells

Cloning Under Conditions of Limiting Dilutions:

Hybrid cells were diluted to one-half cell per well, and 10$^4$ feeder cells per well were added (NS-1 cells were used as feeder cells), and plated together in a 96 well microculture plate with HAT medium. The plates were screened for single cell colony formation and the supernatants tested for specific Ab. To ensure monoclonality the cloning procedure was repeated for a few cycles. The recloned sub-cultures were tested for secretion of specific Ab.

Large Scale Production of Monoclonal Antibodies (McAb)

For large scale production of McAb, the hybridomas can be grown either in vitro in tissue culture conditions, where they secrete up to 1-10 μg McAb/ml; or in vivo as tumors in the peritoneal cavity of mice where they produce up to 1 mg/ml. The main advantage of tissue culture growth is that the hybridoma Ab is the only murine Ab in the tissue culture medium. The advantage of the in vivo system is the large scale production, the cheaper and faster operation and the lower possibility of cell contamination. For these latter reasons we grew the McAb as ascites peritoneal tumor fluid.

Preparation of Ascites:

About one week or longer, before inoculating the cells, the recipient Balb/c mice, were injected IP with 0.5 ml Pristane (2, 6, 10, 14-tetramethyl pentadecane), a mineral oil that creates a proper environment for the growth of hybridomas and myelomas. Five to ten million hybrid cells in 1 ml PBS were injected IP. After a week or longer, enough ascitic fluid accumulated (noticed by the swelling of the belly of mice). The fluid was removed by tapping, that is, insertion of a size 19 hypodermic needle into the lower part of the abdomen. For further transfer of the cells, 0.5 ml of ascites fluid taken just after collection was injected (+PBS) to Pristane treated fresh mice. The suspension was collected, centrifuged and the supernatants titrated by the ELISA assay, to test the level of specific Ab. The clear and tested ascitic fluid was stored frozen at $-20°$ C.

Purification of Antibodies

Monoclonal antibodies can be purified from either culture supernatants or ascitic fluid.

1. Ammonium Sulphate Precipitation of Mouse Ig

Most of the mouse Ig precipitate at 40% saturation of ammonium sulphate at 0° C. We filtered saturated $(NH_4)_2SO_4$, and titrated to pH-7.0. Volume of $(NH_4)_2SO_4$ = volume of serum $\times 0.66$.

After at least one hour at 0° C., the solutions were centrifuged at 10,000 rpm for 15 min., the pellets washed in a solution of 40% saturation ammonium sulphate, centrifuged and resuspended in PBS, following extensive dialysis against PBS. We repeated this procedure once. The optical density (OD) at 280 nm of appropriate dilution for pure IgG. $OD_{280}^{1\%} = 14.5$, therefore IgG (mg/ml) = OD at 280 nm divided by 1.45.

2. Absorptions of Ab by Normal Human Plasma

The absorptions were performed as follows: the sera of the ascitic fluid at a 1:10 dilution in PBS was added to the dry polymer of glutaraldehyde-treated normal human plasma, at a ratio of: 30 mg absorbent to 1 ml of antisera diluted 1:10. The mixture was stirred for 30 min. at 37° C., and for 4 hrs. at 4° C., then was centrifuged twice at 10,000$\times$g for 15 min. at 4° C. and the purified IgG preparation kept at $-20°$ C.

Screening Procedures for Monoclonal Antibodies

The immunoassay used for screening of Ab activity in the hybridomas culture supernatant is a key factor that determines the ultimate success in obtaining the desired McAb. The culture supernatants, the ascitic fluid and, later on, the Ig class of the Ab, were assayed in a variety of tests.

Modified Ouchterlony Assay:

Double diffusion in Agar: The test was performed by pouring molten agar on to glass slides and allowing it to harden. Small wells were punched out of the agar a few millimeters apart. the hybridomas supernatants (-the Ab) and the Ag are placed in opposite wells and allowed to diffuse toward one another in a moist chamber for 24 hours at RT and which immunoprecipitation lines should be formed. This test enabled us to determine the Ig class and subclass.

The enzyme linked immunosorbent assay-ELISA:

This test allows fast evaluation of the results, and selection of positive clones based on a visible observation. ELISA tested the relation between the McAb and the specific Ag (in our case HMTV(47D)-clone 10). This assay is a modification of the Engvall and Perlman technique (Engvall et al., 1972, J. of Immunol. 109: 129-135), and it was performed in NUNC Immunoplates II-96, Nunc Intermed.

Coating of the wells with the Ag:

HMTV (T47D) were used as the Ags for coating 200 μl Ag at the desired concentration (usually 5 or 10 μg/well) diluted in coating buffer were added to the wells; the plates were incubated for two hours at 37° C. Afterwards the plates were washed in a Titertek microplate washer with PBS+0.1% Brij (a detergent).

Addition of the Antibodies:

200 μl of either the hybridomas supernatants, or a 1:50 dilution of the ascitic fluid, were added to the wells at the starting concentration and then diluted with 1:2 up to 1:128, or 1:2 up to 1:3200 respectively. In parallel, 50 μg/ml of the purified IgG was added and diluted 1:2 up to 1.56 μg/ml. The plates were placed at 4° C. overnight. The dilutions were made with PBS-Brij (0.1%)+5% Trasylol.

Addition of the Conjugate:

The plates were washed and the conjugates were added. The conjugates used were: Peroxidase linked rabbit anti mouse IgG (Po-RαMIgG); po-RαMIgM at a 1:2000 dilution. Alternatively, we used alkaline phosphatase linked rabbit anti-mouse IgG (AP-PαMIgG) or goat anti rabbit IgG (APGARIC) (Miles Yeda) at a 1:1000 dilution. The plates were incubated for 2 hours at 37° C.

Preparation of the Alkaline Phosphatase Ig-Conjugate:

The AP-Ig conjugates were prepared with the new McAbs, by the Vollar et al method (Vollar et al., 1976, Bull. WHO 53: 55–65), as follows: (a) 1.4 mg of the IgG in 1.0 ml PBS was added to 5 mg (approximately 5000 units) of the enzyme, mixed at RT, and then dialized extensively overnight against PBS at 4° C.; (b) 25% gluteraldehyde was added to yield a final concentration of 0.2% (v/v), incubated for 4 hours at RT and dialized overnight against PBS with two changes of buffer. The new conjugates were then tritrated by the ELISA test.

Enzymatic Reaction:

After washing the plates, the substrate was added: OPD when the peroxidase conjugate was used, and Sigma 104R for the alkaline phosphatase. The results were measured spectrophotometrically in an automatic scanner Titertek Mutiscan Apparatus (Flow, England) at 492 nm and 405 nm respectively.

The Radioimmunoprecipitation assay:

The antibody preparations were characterized by precipitation of antibody molecules bound to radio iodinated antigen with formaldehyde-fixed staphyloccus aureus (Cowan I strain) as follows:

(1) A radio iodinated Ag (labelled as described by Greenwood et al., 1963, Biochem. J. 89: 114–123) containing about $2 \times 10^6$ cpm was mixed with 100 $\mu$l of the 1 mg/ml absorbed Ab and incubated for 60 min. at 37° C.

(2) One hundred $\mu$l of a 10% formaldehyde inactivated Staphyloccocus aureus was added and incubated for 15 min. at RT.

(3) The complexes were pelleted and washed once with 1M sucrose+TNE (20 mM Tris HCl, 1 mM EDTA and 100 mM NaCl) containing 0.5% NP40 and 0.5% DOC (deoxycholate).

(4) The pellets were then washed several times with TNE containing 0.5% NP40.

(5) The $^{125}$I count in the pellets were monitored in a $\gamma$ scintillation counter.

The Immunohistochemical Assay:

This indirect immunoperoxidase staining was used for detecting the Ag in human breast tumor sections with the McAbs obtained. Several sections from breast and non-breast tissues were prepared from paraffin-embedded blocks, deparaffinized, dehydrated in xylene and graded alcohols, and rinsed in PBS, then incubated with hyalorunidase (Sigma 600 $\mu$/ml) at 37° C. for one hour. After rinsing, each section was incubated overnight with 5 or 10 $\mu$g/ml hybridoma IgG at 4° C. Thereafter the sections were rinsed thoroughly in PBS and incubated with horseradish peroxidase conjugate R$\alpha$MIgG (5–10 $\mu$g/ml IgG) for 30 min. at RT sections were rinsed, treated with 0.04% diaminobenzidine (Sigma) and 0.003% H$_2$O$_2$ for 10 min.; rinsed and counterstained with methylene blue in PBS. The sections were rinsed once more, dehydrated and mounted in permount.

The immunoperoxidase staining procedure has three major advantages: (a) the positive reaction appears as a brown precipitate that, in combination with the appropriate counterstain, provides sufficient histological detail to permit precise cytologic identification and localization; (b) the preparations do not fade and thus can be filed as permanent records for future comparison; (c) paraffin sections can be used if the antigenic determinants of the substance being localized, withstand the routine fixation and embedding procedures required.

Results

Production of Hybridomas

The viability of the fused cells was measured by dividing the viable NS-1 cells by the total number of NS-1 cells.
No. of viable NS-1 cells—$1.6 \times 10^4$
No. of total NS-1 cells—$3.1 \times 10^4$
Viability=$(1.6 \times 10^4/3.1 \times 10^4) \times 100\% = 51.61\%$.
Three weeks after fusion, colonies were observed and grown as described.

The hybridomas obtained were screened for Ig content secreted into the culture media by the Ouchterlony method. The media from the parental hybridomas were assayed by the ELISA test with RMTV (T47D)-clone 10 as the Ags. The parental hybridomas recognized the HMTV (T47D) clone 10.

Cloning of the Hybridomas

The cells of the heterogeneous population of the hybridoma cultures secreting Ig were cloned and single cell sub-cultures obtained. The NS-1 cell line was used as a feeder layer for the cell growth.

Ten days later colonies culture media which recognized (by ELISA) HMTV (T47D)-clone 10 were assayed by the double diffusion test with antisera specific for each of murine immunoglobulin classes. The clones were injected into Balb/c mice in order to obtain large amounts of monoclonal antibodies. Using the ELISA method, the ascitic fluid was tested, starting from a 1:50 dilution. Mouse IgG was purified, as previously described and quantitated.

The McAbs produced by Hyb 23 are of the $\gamma$1 subclass. The McAbs produced by this cell line recognized HMTV (T47D)-clone 10. The McAb Hyb 23 lack reactivity with any retroviruses tested (HMTV, SSV, MPMV, RSV, MULV) nor did they react with human proteins like albumin, immunoglobulin, casein, CEA, hCG. The result confirms that Hyb 23 recognized only the HMTV (T47D)-clone 10, and shows therefore an immunological specific reactivity towards the human mammary tumor virus. Thus, it provides a convenient and specific source of reagent for detection of breast cancer in humans.

The Immunohistochemical Staining on Tissue Sections

Tissue sections of both malignant and benign human mammary tumors, as well as apparently normal tissues, were tested using the indirect immunoperoxidase technique. (Results are shown in Table 1.)

TABLE 1

Indirect Immunoperoxidase Staining of Human Mammary Tissues and Adenocarcinomas to Other Organs with the McAb Hyb 23
Total Cases Tested 478

|  | Positive | Negative |
| --- | --- | --- |
| Normal breast tissue | 0/19 | 19/19 |
| Normal tissue (other than breast) | 0/12 | 12/12 |
| Benign breast tissue | 0/30 | 30/30 |
| Infiltrating duct breast carcinomas | 335/366 | 31/366 |
| Breast metastases to: |  |  |
| lymph node | 15/15 | 0/15 |
| ovary | 5/5 | 0/5 |
| lung | 4/4 | 0/4 |
| bone | 1/1 | 0/1 |
| soft tissue | 1/1 | 0/1 |

TABLE 1-continued

Indirect Immunoperoxidase Staining of Human Mammary Tissues and Adenocarcinomas to Other Organs with the McAb Hyb 23
Total Cases Tested 478

|  | Positive | Negative |
| --- | --- | --- |
| Adenocarcinoma to other organs: | | |
| colon | 0/9 | 9/9 |
| kidney | 0/4 | 4/4 |
| ovary | 0/3 | 3/3 |
| skin | 0/3 | 3/3 |
| thyroid | 0/2 | 2/2 |
| lung | 0/2 | 2/2 |
| prostate | 0/1 | 1/1 |
| liver | 0/1 | 1/1 |

335 cases (91.5% out of 366) of breast cancer tumor sections showed a positive staining reaction in the tumor cells. The staining was shown to be intracellular, cytoplasmic and varied in intensity from cell to cell. The McAb showed no reaction to normal breast tissue from plastic surgery or normal ducts adjacent to tumor cells that showed a positive staining reaction. The Ag was not detected in benign tumor tissues which included fibrocystic disease of the breast, nor in 25 adenocarcinomas to other organs tested, such as adenocarcinoma of the thyroid, adenocarcinoma of the colon, kidney, prostrate, etc. In 15 cases of breast metastases to the lymph nodes, an intense staining reaction in most of the tumor cells was observed. Moreover, when cells from the cell line T47D were embedded in paraffin, blocks and sections prepared, the cells showed a positive reaction with McAbs Hyb 23.

From the results obtained above we can conclude that Hyb 23 detect specifically Ags in breast tumor tissues.

Example 2

Comparison to Rabbit-MMTV gp 52

The gp52 cross-reacting antigen was detected in 62.7% in sections from 204 cases of breast cancer (Keydar et al., 1982, Eur. J. Cancer Clin. Oncol. 18(12): 1321-1328) using IgG from rabbit immunized with purified gp52. Patients born in North Africa were found containing significantly higher presence of antigen (80%). The Results also indicate that the frequency of the demonstration of the gp52 cross-reacting antigen is higher when the patients are in the advanced stage of the disease, suggesting a correlation between the severity of the disease and detectability of the antigen.

Our McAb, Hyb 23 detected HMTV antigen in breast cancer biopsies in more than 91% of 366 cases. Normal and benign breast tissues as well as other malignancies tested did not show any positive reactions whatsoever. Hyb 23 has been proven extremely useful in the immunohistochemical identification of metastatic breast lesions in patients with no clinical evidence of a primary breast carcinoma or in whom the possibility of a second primary carcinoma must be considered. In 26 such cases tested, Hyb 23 has identified the lesions as metastases from primary breast carcinomas.

Example 3

Detection of HMTV (T47D)-Clone 10-Related Antigen in Body Fluids

The T47D cell line and its subclones contain, in the cytoplasm and on cell surface a human cancer antigen immunologically reacting with Hyb 23. In this respect, the cell line mimics the human breast tumor tissue. Since McAbs Hyb 23 recognized the specific antigen in both viral particles and in soluble protein shed-off into the growth medium by T47D-clone 10 cells in vitro, it was very likely to find similar situation in vivo. Obviously the development of a sensitive method for assaying the level of the HMTV (T47D) clone-10 antigen in body fluids will be of great help in the detection and assessment of the malignant process in the human neoplasia.

Indeed, the presence of significantly high levels of the HMTV (T47D)-clone 10-related antigen, recognized by Hyb 23, was demonstrated in sera as well as in both pleural and ascitic fluids from breast cancer patients. On the other hand, low levels of this antigen could be detected in fluids from either apparently healthy humans or from patients with malignancies other than adenocarcinoma of the breast.

The presence of the antigen was analyzed by two independent methods:

A. Radioimmune-Assay

The ability of the sera of breast cancer patients to react with Hyb 23 was monitored by tracing the labeled antigen-antibody complexes using 125-I labeled plasma proteins. The results of the experiment show that substantially more 125-I labeled antigen from breast cancer patients' plasma were bound to Hyb 23 (5.2-fold) than with the control serum, although significant non-specific binding also occurred.

TABLE 2

Radioimmune assay of human plasma with various antibodies

|  | IgG bound (cpm) | | | |
| --- | --- | --- | --- | --- |
|  | Breast cancer patients plasma | | Normal human plasma | |
| Antibodies | | | | |
| I-labeled plasma | total | net | total | net |
| Control mouse ascites | 8950 | — | 5100 | — |
| Hyb 23 | 21500 | 12550 (5.2)* | 7510 | 2410 |
| Preimmune rabbit IgG | 7400 | — | 6200 | — |
| Rabbit anti HMTV (T47D) clone 10 | 13200 | 5800 (4.1)* | 7600 | 1400 |

*The figure in parentheses represent the ratio of net cpm obtained with breast cancer patients' serum to net counts obtained with normal human serum.

B. Enzyme-Linked Immunosorbent Assay (Elisa)

This assay was designed for detection and determination of HMTV (T47D)-clone 10 antigen in human sera. This assay is a modification of the Engvall and Perlman technique (Engvall et al., 1972, J. of Immunol. 109: 129–135), and it was performed in NUNC Immunoplate II-96, Nunc Intermed.

1. Coating the well with the McAb:

Hyb 23, IgG γ1 directed against HMTV (T47D)-clone 10 were used as the Ab for coating. 200 μl of 5 μg of IgG per ml in carbonate buffer pH 9.6 were added to the wells; the plates were incubated for 2 hours at 37° C. and afterwards the plates were washed in a Titertek microplate washer with PBS+0.1% Brij (a detergent). Precoated plates were kept at 4° C. until use.

2. Addition of the patients' sera:

Dilutions of the sera in PBS-Brij (0.1%)+5% Trasylol are added to the wells and the plate were placed at 4° C. overnight and then washed 4 times with the same buffer.

3. Addition of the conjugate and the enzymatic reaction:

The conjugate in appropriate dilutions was added to the wells. The plates were incubated for 2 hours at 37° C.

After washing the plate, the substrate was added (Sigma 104R). The reaction product was measured spectrophotometically in an automatic scanner (Titretek Multiscan Apparatus, Flow, England) at 405 nm.

The absorbance at 405 nm represents the amount of the product of the enzymatic reaction and therefore indirectly reflects the level of antigen bound by the McAbs.

The controls used in each plate:

1. HMTV (T47D)-clone 10 reconstructed in human, apparently normal, sera at initial concentration of 5 µg/ml as positive control.
2. Sera from human, apparently, normal, donors as negative control.
3. Ascites from non-relevant monoclonal antibody (same subclass IgG γl) directed against non-relevant antigen, as a control for non-specific binding of antigen. This non-relevant McAbs (control McAb) were used as coating Abs instead of Hyb 23.

This "sandwich" immunometric assay technique for determination of the presence and concentration of HMTV (T47D)-clone 10-related antigen in sera of human patients can be used either with the same monoclonal antibodies or with two different antibodies.

One antibody is presented in a soluble labeled form (the conjugate) and a second unlabeled antibody is presented bounded to the solid support (the coating antibody). The soluble and bound antibodies may be the product of either the same or different hybridoma clones (McAbs).

Furthermore, the availability of the monoclonal antibodies provides a way for the development of a heterologous immunoassay in which one of the antibody used in our "sandwich" assay is affinity purified rabbit antibodies against HMTV (T47D)-clone 10. It can be simultaneously used, with our Hyb 23 monoclonal antibody, as the coating antibody or as the soluble labeled antibody, thus attaining the sensitivities required for our assay.

The levels of the specific antigen in the different sera were calculated from the absorbance at 405 nm, and expressed as an Index, according to the following formula:

$$\text{Index} = \frac{A - A_o}{V - V_o}$$

where:
A—Absorbance with serum sample in wells precoated with Hyb 23 Abs.
Ao—Absorbance with the same serum in wells precoated with control McAbs.
V—Absorbance with reconstructed HMTV (T47D) clone-10 sample in wells precoated with Hyb 23 Abs.
Vo—Absorbance with reconstructed HMTV (T47D) clone-10 sample in wells precoated with control McAbs.

Analyses of sera samples from about 300 apparently healthy women led to the conclusion that a cut-off Index of 0.25 is suitable to distinguish between the sera with a significant positive level of antigen and those which were negative for antigen.

RESULTS

1. Out of the patients with advanced metastatic breast cancer 70% showed positive antigen levels in their sera or pleural effusions (Index>0.25), whereas only 30% were apparently false negative (Index<0.25).
2. 83% out of 264 apparently normal women showed negative levels of antigen in their sera (Index<0.25). Therefore 17% were apparently false positive. It is of course of the highest interest to follow the clinical status of these women, in order to determine whether the appearance of this antigen is a reliable early prognostic marker for a development of breast adenocarcinomas in the future.
3. In a small group of breast cancer patients we were able to demonstrate changes in the antigen levels in parallel with or even prior to clinical manifestation of the disease (i.e., increase in Index along with clinical deterioration, or decrease in Index in patients responding to cancer treatment).

Thus, the HMTV (T47D)-clone 10-related antigen can be determined bu ELISA in an accurate, non-invasive and sensitive assay, using McAbs Hyb 23.

What is claimed is:

1. The hybridoma cell line having ATCC Accession No. HB 8630 which results from the fusion of
   spleen cells of Balb/c mice immunized with human mammary tumor virus particles derived from T47D clone-10, and
   NS-1 non-producing immunoglobin myelomas derived from Balb/c mice.

2. The monoclonal antibody which recognizes human mammary tumor virus-like particles derived from T47D clone-10 breast cancer cell line and which is produced and secreted by the hybridoma cell line of claim 1 wherein said monoclonal antibody is characterized by a high percent accuracy of recognition reaching up to 90% to 100% of all breast metastases, without significant undesirable false positives or cross reactions with malignancies of non-breast origin.

3. An immunoassay for diagnosing and monitoring human breast cancer, wherein said immunoassay is characterized by the use of monoclonal antibodies having a high percent accuracy of recognition reaching up to 90% to 100% of all breast metastases, without significant undesirable false positives or cross reactions with malignancies of non-breast origin, comprising:
   contacting a sample with first and second antibodies to form an antibody-antigen complex with any human mammary tumor virus contained in said sample, one of said first and second antibodies being detectable and the other being the monoclonal antibody produced and secreted by hybridoma cell line ATCC Accession determining the presence or absence of detectable antibody in said antibody-antigen complex.

4. An immunoassay according to claim 3, wherein said detectable antibody is linked to an enzyme which catalyzes a detectable reaction.

5. An immunoassay according to claim 4, wherein said enzyme is alkaline phosphatase or horseradish peroxidase.

6. An immunoassay according to claim 3, wherein said detectable antibody is radioactively labeled.

7. An immunoassay according to claim 6, wherein said antibody is labeled with $^{125}I$.

8. An immunoassay according to claim 3, wherein said sample is a tissue sample and wherein said first antibody is said monoclonal antibody and said second antibody is detectable and directed to said monoclonal antibody.

9. An immunoassay according to claim 8, wherein said tissue sample is breast tissue.

10. An immunoassay for diagnosing and monitoring human breast cancer, wherein said immunoassay is characterized by the use of monoclonal antibodies having a high percent accuracy of recognition reaching up to 90% to 100% of all breast metastases, without significant undesirable false positives or cross reactions with malignancies of non-breast origin, comprising:
 contacting a tissue sample with monoclonal antibody derived from hybridoma cell line ATCC Accession No. HB 8630 to form an antibody-antigen complex between the monoclonal antibody and any human mammary tumor virus contained in said tissue sample;
 thereafter contacting said tissue sample with a detectable antibody directed to said monoclonal antibody; and
 determining the presence or absence of detectable antibody in said complex.

11. An immunoassay according to claim 10, further comprising the step of separating said tissue sample from unreacted antibody prior to detecting said tissue sample with said detectable antibody.

12. An immunoassay according to claim 11, wherein said detectable antibody is radioactively labeled.

13. An immunoassay according to claim 12, wherein said antibody is labeled with $^{125}I$.

14. An immunoassay according to claim 11, wherein said detectable antibody is an antibody linked to an enzyme which catalyzes a detectable reaction.

15. An immunoassay according to claim 14, wherein said enzyme is alkaline phosphatase or horseradish peroxidase.

16. An immunoassay according to claim 14, wherein said detectable antibody is rabbit anti-mouse immunoglobin linked to an enzyme which catalyzes a detectable reaction.

17. An immunoassay according to claim 16, wherein said detectable antibody is a conjugate of horseradish peroxidase and rabbit anti-mouse immunoglobin or a conjugate of alkaline phosphatase and rabbit anti-mouse immunoglobin.

18. An immunoassay for diagnosing and monitoring human breast cancer, wherein said immunoassay is characterized by the use of monoclonal antibodies having a high percent accuracy of recognition reaching up to 90% to 100% of all breast metastases, without significant undesirable false positives or cross reactions with malignancies of non-breast origin, comprising:
 contacting a fluid sample with a first soluble antibody to form an antibody-antigen complex with any human mammary tumor virus contained in said sample, said first antibody being detectable;
 contacting said complex with a second antibody to said human mammary tumor virus, said second antibody being attached to a solid matrix, and one of said first or second antibodies being the monoclonal antibody produced and secreted by hybridoma cell line ATCC Accession No. HB 8630; and
 detecting or measuring the presence or absence of detectable antibody in said complex.

19. An immunoassay according to claim 18, wherein said solid matrix is separated from said fluid sample and said first antibody prior to said detecting or measuring step.

20. An immunoassay according to claim 9, wherein said first antibody is said monoclonal antibody and said second antibody is affinity purified rabbit antisera against human mammary tumor virus produced by the T47D clone-10 cell line.

21. An immunoassay according to claim 19, wherein said first and second antibodies are monoclonal antibodies.

22. In an immunoassay for diagnosing human breast cancer, wherein said immunoassay is characterized by the use of monoclonal antibodies having a high percent accuracy of recognition reaching up to 90% to 100% of all breast metastases, without significant undesirable false positives or cross reactions with malignancies of non-breast origin, comprising contacting a sample with first and second antibodies to form an antibody-antigen complex with any human mammary tumor virus contained in said sample, wherein one of said antibodies is labeled and at least one of said antibodies is a monoclonal antibody which recognizes said human mammary tumor virus and determining the presence or absence of detectable antibody in said complex, the improvement comprising using as said monoclonal antibody the monoclonal antibody produced and secreted by hybridoma cell line having ATCC Accession No. HB 8630.

* * * * *